United States Patent
Shen et al.

(10) Patent No.: US 10,624,536 B2
(45) Date of Patent: Apr. 21, 2020

(54) VIRTUAL REALITY-BASED OPHTHALMIC INSPECTION SYSTEM AND INSPECTION METHOD THEREOF

(71) Applicants: Ho-Fang Shen, Taipei (TW); Ming-Fu Chen, Taipei (TW)

(72) Inventors: Ho-Fang Shen, Taipei (TW); Ming-Fu Chen, Taipei (TW)

( * ) Notice: Subject to any disclaimer, the term of this patent is extended or adjusted under 35 U.S.C. 154(b) by 24 days.

(21) Appl. No.: 16/000,668

(22) Filed: Jun. 5, 2018

(65) Prior Publication Data

US 2018/0344148 A1 Dec. 6, 2018

(30) Foreign Application Priority Data

Jun. 6, 2017 (TW) .............................. 106118619 A

(51) Int. Cl.
*A61B 3/032* (2006.01)
*A61B 3/00* (2006.01)
*A61B 3/10* (2006.01)

(52) U.S. Cl.
CPC .............. *A61B 3/032* (2013.01); *A61B 3/005* (2013.01); *A61B 3/0025* (2013.01); *A61B 3/0033* (2013.01); *A61B 3/10* (2013.01)

(58) Field of Classification Search
CPC ..... A61B 3/0025; A61B 3/103; A61B 3/1015; A61B 3/14; A61B 3/10
USPC ........................................................ 351/205
See application file for complete search history.

(56) References Cited

U.S. PATENT DOCUMENTS

| 2011/0285960 A1* | 11/2011 | Kohn ....................... G02C 7/02 351/159.74 |
| 2012/0050685 A1 | 3/2012 | Artlett et al. |
| 2014/0176528 A1* | 6/2014 | Robbins ............... G02B 27/225 345/419 |
| 2016/0324416 A1 | 11/2016 | Fateh |

(Continued)

FOREIGN PATENT DOCUMENTS

| CN | 202843576 U | 4/2013 |
| CN | 205903239 U | 1/2017 |

OTHER PUBLICATIONS

Office Action dated Jan. 19, 2018 of the corresponding Taiwan patent application No. 106118619.

(Continued)

*Primary Examiner* — Mohammed A Hasan
(74) *Attorney, Agent, or Firm* — Chun-Ming Shih; HDLS IPR Services

(57) ABSTRACT

A virtual reality-based ophthalmic inspection system includes a wearable unit, an electronic unit, and at least one detector; the wearable unit is available for an inspected object to wear the wearable unit on head; the electronic unit is assembled with the wearable unit and has a left-eye display zone and a right-eye display zone, wherein the left-eye display zone is used for displaying at least one left-eye sight-targets, and the right-eye display zone is used for displaying at least one right-eye sight-targets; the detector is disposed on the electronic unit. A sight-target with at least one distinguishing feature are shown on one of the left-eye display zone and the right-eye display zone, the left-eye display zone displays the sight-target while the right-eye display zone is filled with black, and the right-eye display zone displays the sight-target while the left-eye display zone is filled with black.

17 Claims, 10 Drawing Sheets

(56) References Cited

U.S. PATENT DOCUMENTS

2016/0353987 A1* 12/2016 Carrafa ................. A61B 3/032
2018/0008141 A1* 1/2018 Krueger ................ A61B 5/744

OTHER PUBLICATIONS

Office Action dated Mar. 29, 2018 of the corresponding Taiwan patent application No. 106118619.
Office Action dated May 23, 2018 of the corresponding Taiwan patent application No. 106118619.

* cited by examiner

VIRTUAL REALITY-BASED OPHTHALMIC INSPECTION SYSTEM AND INSPECTION METHOD THEREOF

BACKGROUND

Technical Field

The present disclosure relates to an optometry system and an optometry method and, more particularly, to a virtual reality-based ophthalmic inspection system and inspection method thereof.

Description of Related Art

An eye chart (or called acuity chart, optotype) is used for measuring the ability of a visual system to recognize the fine structure of the object (or the spatial resolution of the visual system). It represents the most common and useful test for inspecting visual function; it may further used to determine the lens correction associated with ocular defects. In general, the viewing distance of six meters is called far acuity, and the apparatus is called far acuity chart. Hence, six meters (or 20 feet) are considered optical infinity when person's viewing distance is approximately 6 meters at rest condition.

The visual acuity of the inspected object is identified b by the smallest optotype on the eye chart seen by the inspected objected away from the eye chart with a predetermined distance, quantified optotype size, and quantified illuminant condition. The optotypes are usually letters, numbers, or geometric symbols.

However, the inspection mentioned above requires substantial space and the inspected object cannot perform the inspection by himself/herself.

SUMMARY

According to one innovative aspect of the subject matter in this specification can be embodied in a virtual reality-based ophthalmic inspection system. The system includes a wearable unit, an electronic unit, and at least one detector. The wearable unit is available for an inspected object to wear on head. The electronic unit is assembled with the wearable unit and has a left-eye display zone and a right-eye display zone, the left-eye display zone is used for displaying at least one left-eye sight-target, and the right-eye display zone is used for displaying at least one right-eye sight-target. The detector is disposed on the electronic unit. A sight-target with at least one distinguishing feature is shown on one of the left-eye display zones and the right-eye display zone. The left-eye display zone displays the sight-target while the right-eye display zone is filled with black, and the right-eye display zone displays the sight-target while the left-eye display zone is filled with black.

In an embodiment of the present disclosure, a size of the sight-target is successively increased before the detector captures a predetermined indication. After the detector received the predetermined indication, the distinguishing feature of the sight-target is changed step by step while the size of the sight-target is fixed at a specific size. The detector further captures distinguishing features to identify the eyesight information which relates the distinguishing features of the sight-targets successively displayed on the left-eye display zone or the right-eye display zone, and a visual acuity of the inspected object is identified according to mentioned eyesight information.

In an embodiment of the present disclosure, the specific size is the size that displayed on the electronic unit while the detector captures the predetermined indication.

In an embodiment of the present disclosure, the specific size is the size that displayed on the electronic unit of a previous predetermined time period during which the predetermined indication is received.

In an embodiment of the present disclosure, the left-eye display zone or the right-eye display zone may display a plurality of sight-targets whose contrast varies from high to low for inspecting visual sensitivity.

When measuring eyesight, screen brightness directly affects the accuracy. However, the brightness of each manufacturer's production screen is different, resulting in the same visual acuity with different test results. Hence, the "calibration process" of screen brightness and color temperature is necessary. The calibration process refers to checking the phone model and the screen model when the eyesight measurement software is started. Then the backlight brightness is adjusted according to the models of the phones and the models of the screens for the most suitable measurement condition. The process guarantees the same brightness and the same color temperature for each measurement. In addition, the process can prevent the blue light of the screen from causing eye damage, and can maintain the accuracy in the color discrimination test.

In an embodiment of the present disclosure, the system may perform a background calibration procedure for adjusting the illuminant and optimizing color temperature of the display unit.

In an embodiment of the present disclosure, the sight-target initially displayed on the left-eye display zone and the right-eye display zone is from the smallest size.

In an embodiment of the present disclosure, the sight-target is selected from a set of letters consisting essentially of capital bold character E in a Berlin Sans FB font, capital character C in a Bauhaus 93 font, and lowercase character C in a Vrindab font for the best performances.

In an embodiment of the present disclosure, the system may further display an Amsler grid on one of the left-eye and the right-eye display zones, wherein the Amsler grid comprises equally spaced, parallel horizontal lines, vertical lines, and a center point, the horizontal lines and the vertical lines collectively form a plurality of intersections, and the center point is the geometric center of the Amsler grid. However, it is hard to identify the eyesight distortion area in virtual reality environments. By dichotomizing selection to narrow down areas of the left-eye or the right-eye display zone, brightness can be used to mark the portion of the distortion or unseen area.

According to one innovative aspect of the subject matter in this specification can be embodied in an ophthalmic examination method. The method includes the following: providing a display unit comprising a left-eye display zone and a right-eye display zone; display a sight-target on one of the left-eye display zone and the right-eye display zone, wherein the sight-targets has an initial distinguish feature and an initial size; successively increasing the size of the sight-target while the distinguish feature being fixed; capturing a predetermined indication; and successively changing the distinguish features of the sight-target while the size of the sight-target being fixed at a specific size and capturing eyesight information in relation to the distinguishing features.

In an embodiment of the present disclosure, the method further includes the following: determining whether both eyes visual acuity inspection being finished; displaying the sight-target on one of the left-eye display zone or the right-eye display zone, wherein the sight-targets has the initial distinguish feature and the initial size; successively increasing the size of the sight-target until capturing a predetermined indication to make the distinguish feature fixed; and successively changing the distinguish features of the sight-target while the size of the sight-target being fixed at a specific size and capturing eyesight information based on users' response in relation to those distinguishing features.

In an embodiment of the present disclosure, the method further includes the following: identifying a visual acuity according to the distinguishing features which response to eyesight information.

In an embodiment of the present disclosure, the method further includes the following: storing the distinguishing features which response to eyesight information and the information provides ophthalmologists or optometrists identifying the visual acuity.

In an embodiment of the present disclosure, the method further includes the following: displaying a plurality of sight-targets arranged in line whose contrast varies from high to low on one of the left-eye display zone and the right-eye display zone for inspecting visual sensitivity. In an embodiment of the present disclosure, the method further includes the following: displaying an Amsler grid on one of the left-eye and the right-eye display zones, wherein the Amsler grid comprises equally spaced, parallel horizontal lines, vertical lines, and a center point, the horizontal lines and the vertical lines collectively form a plurality of intersections, and the center point is the geometric center of the Amsler grid; identifying the portion of the Amsler grid that the inspected object sees as distorted or unseen by capturing the predetermined indication to dichotomizing the display zone by contrast or brightness differences; and continuously apply the dichotomizing method to narrow down location until the distorted and unseen area to identify.

In an embodiment of the present disclosure, the method further includes the following: performing a background display calibration procedure for adjusting the illuminant and optimizing color temperature of the display unit.

BRIEF DESCRIPTION OF DRAWING

The present disclosure can be more fully understood by reading the following detailed description of the embodiment, with reference made to the accompanying drawings as follows.

DETAILED DESCRIPTION

Figure 1:
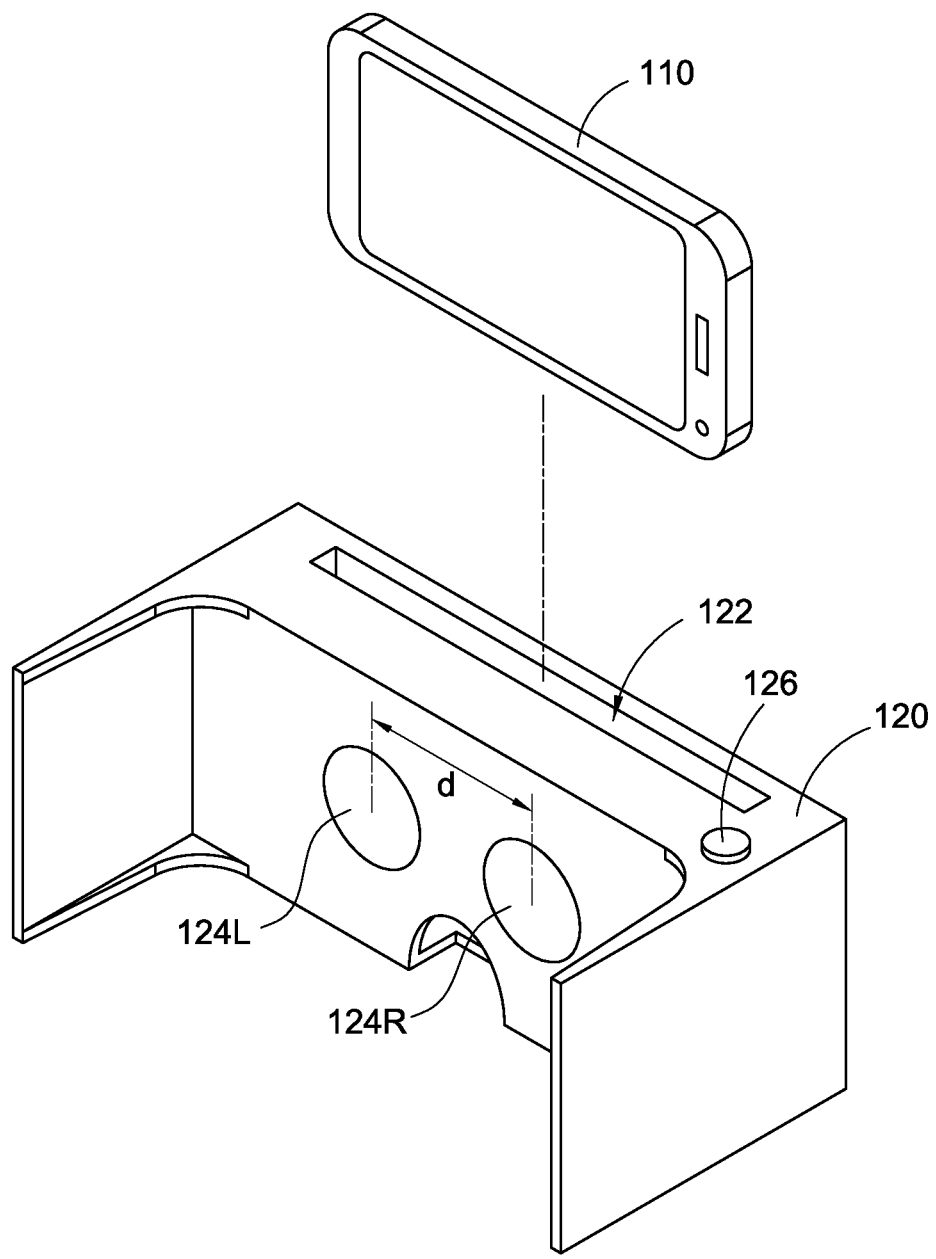
FIG. 1 depicts a schematic diagram illustrating a virtual reality-based ophthalmic inspection system in accordance with the present disclosure.
Figure 2:
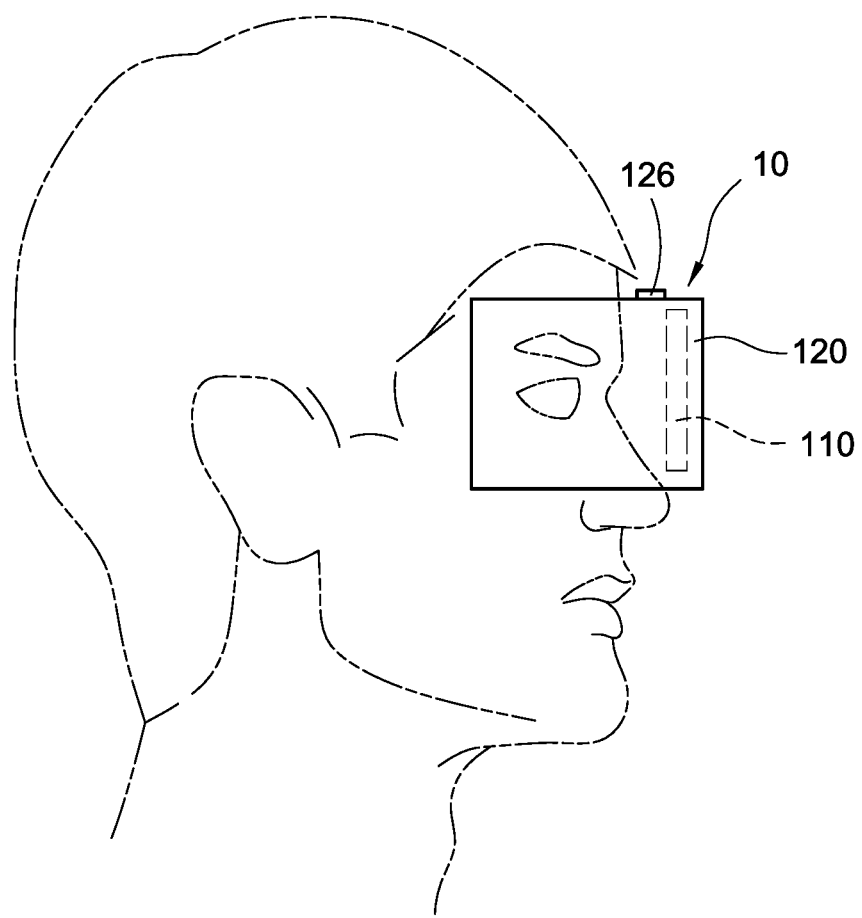
FIG. 2 depicts a schematic diagram illustrating the operation of the virtual reality-based ophthalmic inspection system in accordance with the present disclosure.

FIG. 1 is a schematic view of a virtual reality-based ophthalmic inspection system in accordance with the present disclosure, and FIG. 2 is a schematic view of the operation of the virtual reality-based ophthalmic inspection system in accordance with the present disclosure. The virtual reality-based ophthalmic inspection system 10 includes an electronic unit 110 and a wearable unit 120, and the electronic unit 110 is affixed to the wearable unit 120. The virtual reality-based ophthalmic inspection system 10 is wearable on a user's head, and the electronic device 110 corresponding on the user's eye is configured to display images (of eye sights). The electronic unit 110 is, for example, a smartphone. In FIG. 1, the electronic unit 110 and the wearable unit 120 are separated; in the other words, the electronic unit is treated as a smartphone during the electronic unit 110 is not affixed to the wearable device 120. However, in the other embodiment, the electronic unit 110 and the wearable unit 120 may be integrated-formed, i.e., the electronic unit 110 and the wearable unit 120 collectively form a headset electronic unit, which cannot be detached.

In FIG. 1, a front end of the wearable unit 120 forms an installation slot 122, the electronic unit 110 is installed in the wearable unit 120 through the installation slot 122. The wearable unit 120 further includes two lenses 124 and 124L, which may be placed at a rear end of the wearable unit 120; the focal lengths of the lenses 124R and 124L are designed for clearly imaging the light emitted from the electronic unit 110 on user's retinas. The lenses 124R and 124L may convert light emitted from the electronic unit 110 to a parallel light, and the parallel light is then transmitted to user's eyes that have normal vision. In operation, the rear end of the wearable unit 120 may attach to user's face, and user's eyes view the images shown on the electronic unit 110 through the lenses 124R and 124L.

During an eye inspecting process, the virtual reality-based ophthalmic inspection system 10 may simulate the situation in which the inspected object covers one eye when performing visual acuity inspection on the other eye; in the other words, the virtual reality-based ophthalmic inspection system 10 is configured to inspect monocular visual acuity.

Figure 3:
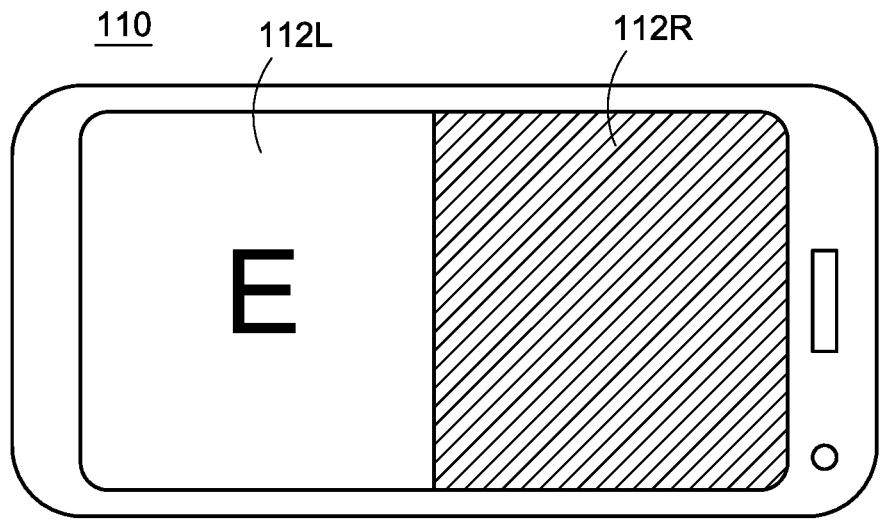
FIGS. 3-5 depict schematic diagrams illustrating eye sights shown on a display for inspecting visual acuity of left eye.
Figure 4:
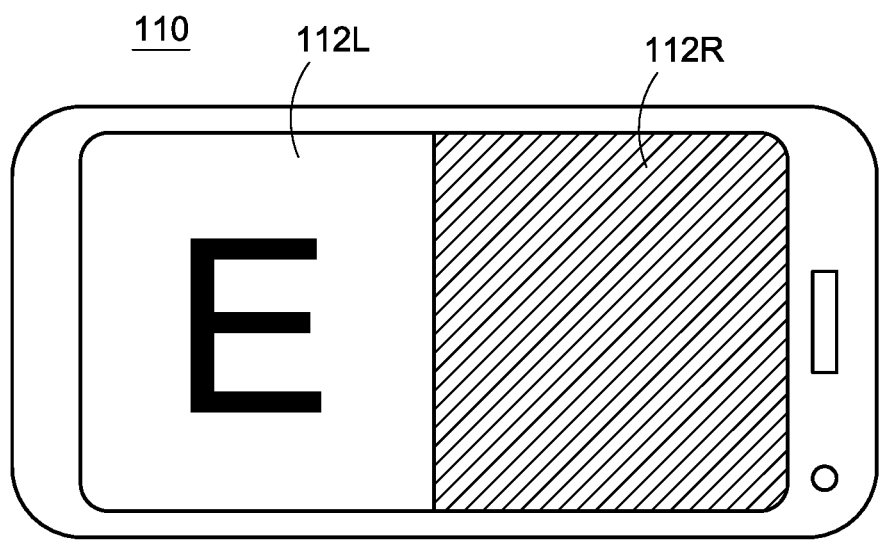
Figure 5:
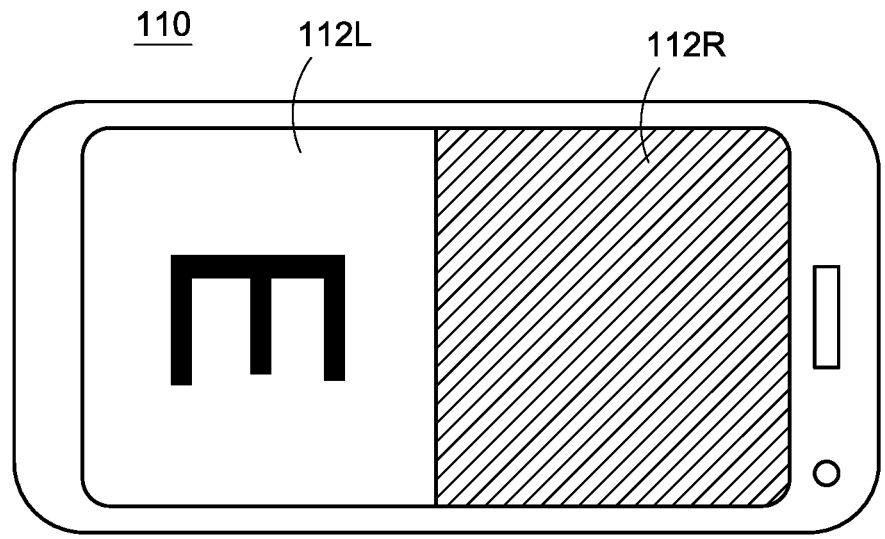
Figure 6:
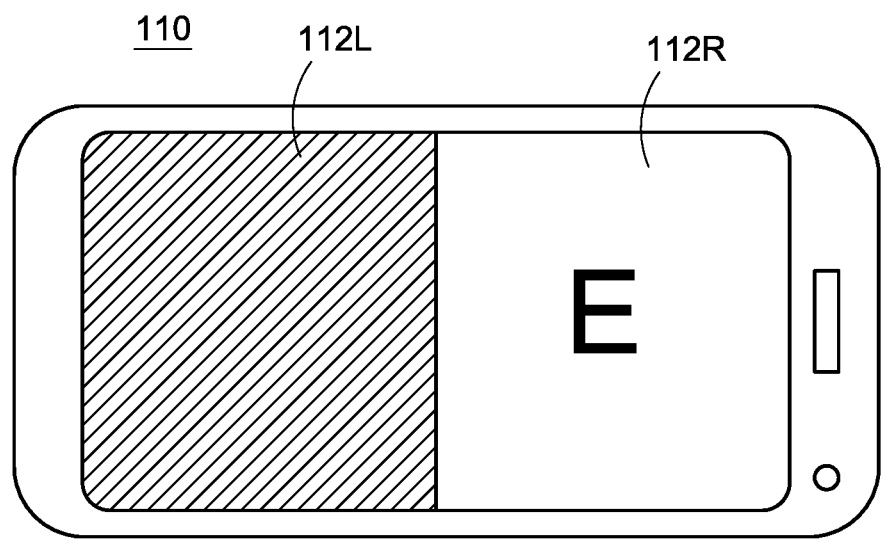
FIGS. 6-7 depict schematic diagrams illustrating eye sights shown on the display for inspecting visual acuity of right eye.
Figure 7:
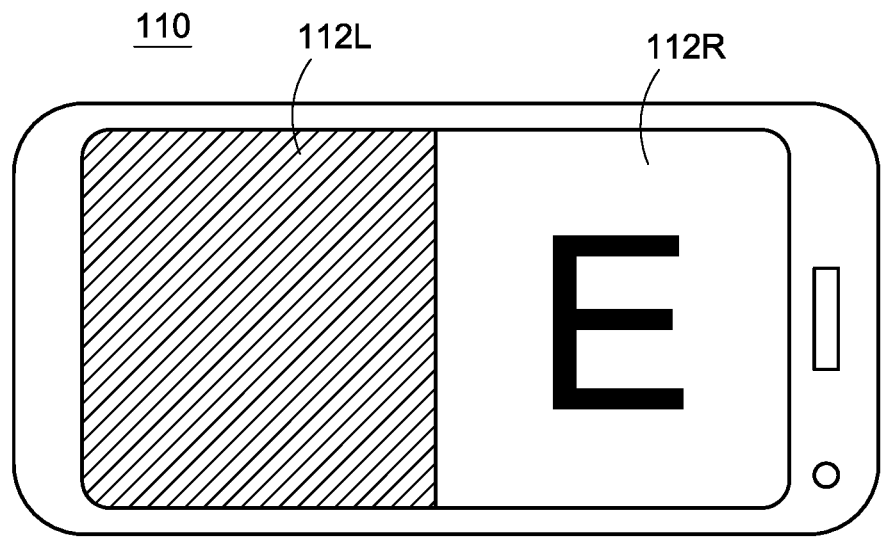

Specifically, the electronic unit 110 includes a display unit 112, which is divided into a right-eye display zone 112R for right eye viewing and a left-eye display zone 112L for left eye viewing. During left eye inspecting process, the left-eye display zone 112L displays the sight-target(s); the right-eye display zone 112R does not display any sight-targets and is filled with black (the diagonal lines showed in FIG. 3 to FIG. 5 represent the right-eye display area 112R filled with black) to simulated the situation which the inspected persons covers right eye when performing visual acuity inspection on the left eye; wherein the right-eye display zone 112R filled with black is used for complete blocking the vision of right eye. Similarly, during right eye inspecting process, the right-eye display zone 112R displays the sight-target(s); the left-eye display zone 112L does not display any sight-target and is filled with black (the diagonal lines showed in FIG. 6 to FIG. 7 represent the left-eye display area 112L filled with black) for completely blocking the vision of left eye. In addition, the distance between the lenses 124R and 124L is designed to prevent the image for one eye viewing from viewing by the other eye.

Figure 8:
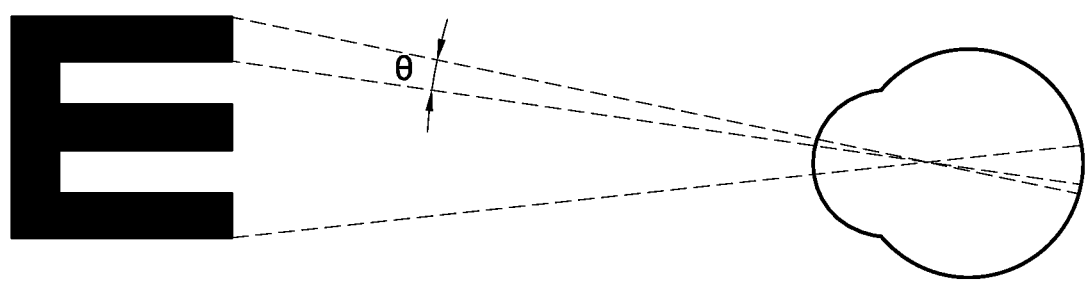
FIG. 8 depicts the principle for inspecting the visual acuity.

Visual acuity is often inspected according to the size of the sight-targets viewed on display unit 112. The sight-targets may be letters, numbers, images, geometric symbols or other acceptable sight-targets having a distinguish feature. The distinguish feature enables the person with the visual acuity of 1.0 to identify (the shape, the opening, or the direction) of the sight target. Notably, a person with visual acuity of 1.0 represents he/she can clearly identify the sight-targets having a threshold visual angle of 1 minute, i.e., the minimum angle of resolution (MAR) thereof is 1 minute, as shown in FIG. 8.

In the present disclosure, the sight-target is selected from a set of letters consisting essentially of capital bold character E in a Berlin Sans FB font, capital character C in a Bauhaus 93 font, and lowercase character C in a Vrindab font. The following takes the sight-target "E" as an illustrated example, and the distinguish feature thereof is the orientations of the sight-target "E". As shown in Table 1, the size (or called "the point") of the sight-target corresponds to different visual acuity for eye. In Table 1, the sight-target with 1 point corresponds to visual acuity of 1.2; in detail, during the inspection, if the person clearly views the sight-target with 1 point on the display 112, the inspected (right or left) eye has the visual acuity of 1.2.

TABLE 1

| | size of sight-target | | | | | | | | |
|---|---|---|---|---|---|---|---|---|---|
| | 10 | 9 | 8 | 7 | 5 | 4 | 3 | 2 | 1 |
| visual acuity | 0.1 | 0.2 | 0.4 | 0.5 | 0.6 | 0.8 | 0.9 | 1.0 | 1.2 |

In an embodiment, the electronic device 110 may have a resolution of at least 2560×1440 pixels for preventing the sight-target "E" from edge blurred or lines and spaced of the sight-target "E" displayed unevenly. Furthermore, the illuminance of the electronic device 110 is designed to follow the standard protocols, for example, 200±120 cd/m², and the contrast between the sight-target and the background of the sight-target may be designed as 0.9±0.05 to enhance inspection accuracy. In the embodiment, the sight-target is black, while the background is white.

Notably, in some embodiments, the brightness and color of the background may be changed according to different inspection requirement. Specifically, the brightness of the display unit 112 may directly affect the inspection accuracy; however, the display unit 112 fabricated by different foundries may have different brightness, which makes the software for performing the inspection cannot provide the same inspection result and lower the inspection accuracy. As such, a calibration procedure to adjust the brightness and color temperature of the display unit 112 when the software is activated is desired. The calibration procedure may measure the type of the electronic unit 110 or the display unit 112, and then adjust and maintain the background brightness of the display unit 112. Besides, the calibration procedure may further optimize the color temperature of the display unit 112 for reducing blue irradiation.

In the present disclosure, the size of sight-target is successively increased during the visual acuity inspection, and the right eye and the left eye are independently inspected. In an embodiment, the virtual reality-based ophthalmic inspection system 10 may inspect the visual acuity of the left eye (by the sight-target shown in FIG. 3 to FIG. 5) prior to inspecting the visual acuity of the right eye (by the sight-target shown in FIG. 6 and FIG. 7). In the other embodiment, the virtual reality-based ophthalmic inspection system 10 may inspect the visual acuity of the right eye prior to inspecting the visual acuity of the left eye.

In detail, the electronic device 110 may initially display the sight-target with size of 1 on the display unit 112 and successively increase the size of the sight-target according to Table 1. For example, the display unit 112 display the sight-target shown in FIG. 3 which smaller size firstly, and then display the sight-target shown in FIG. 4 until the inspected object provides a predetermined indication by at least one of body movements (such as gesture, finger motions or nod) and voice to accomplish a preliminary inspection. The display period of the sight-target with different size may be designed to simulate the visual effect that the sight-target toward the inspected object's sight. Thereafter, an advanced inspection may be further performed to identify the visual acuity of the inspected object. During the advance inspection, the electronic unit 110 may display the sight-target with different distinguish features while the size thereof is fixed at a specific size for several times (for example, two or three times), and performing the visual acuity inspecting procedure by the question and answering for enhancing the accuracy.

Figure 9A:
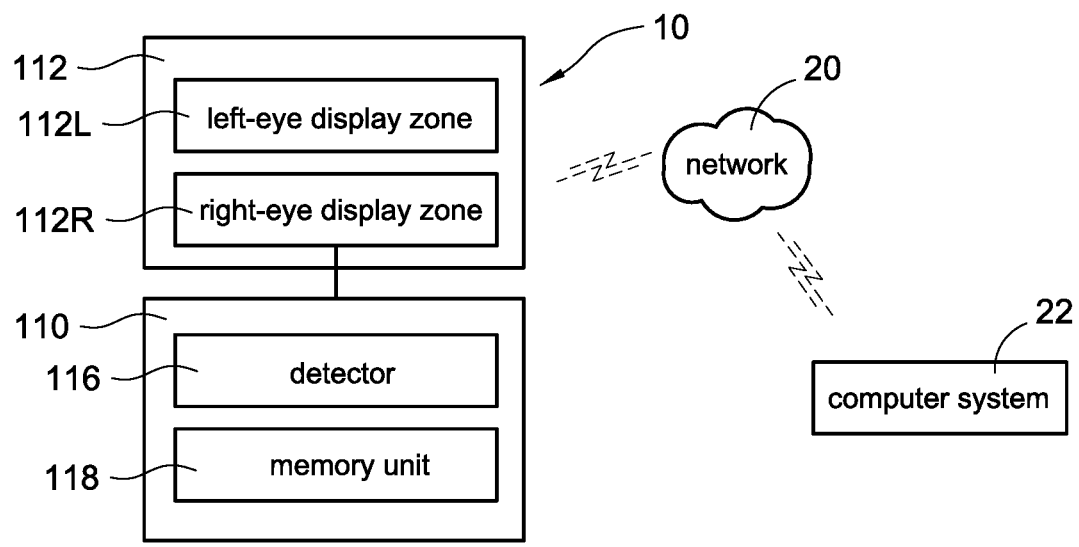
FIGS. 9A-9B depict system block diagrams illustrating the virtual reality-based ophthalmic inspection system in accordance with the present disclosure.
Figure 9B:
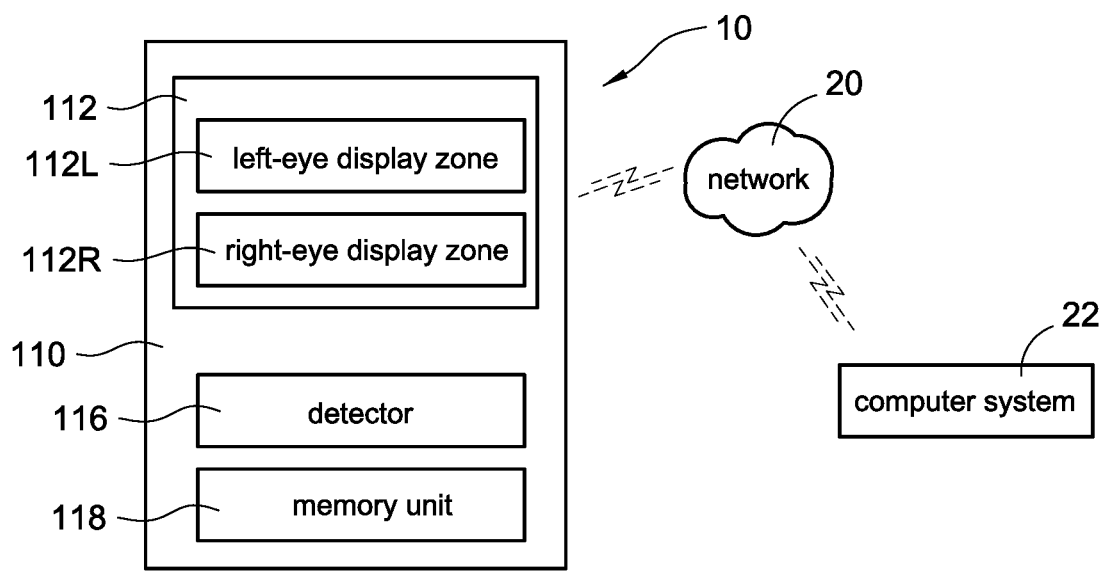

In should be noted that the virtual reality-based ophthalmic inspection system 10 may further include a detector 116 (as shown in FIG. 9A and FIG. 9B) for capturing the predetermined indication including at least one of body movements and voice. The detector 116 may be one of a button, a microphone, a camera, an ambient light sensor, a gyroscope, and a three-dimensional accelerometer, which may be the component(s) of the electronic unit 110. When the electronic unit 120 and the wearable unit 120 are separated, the wearable unit 120 may have hole(s) (not shown) at the position where the microphone, the camera, and the ambient light sensor are disposed for capturing the predetermined indication; the circuit block diagram of the system 10 which the electronic unit 120 and the wearable unit 120 are separated is shown in FIG. 9A. When the electronic unit 120 and the wearable unit 110 are integrated-formed, the detector 116 may be disposed on the wearable unit 120 and the electrically connected to the electronic unit 110 as shown on FIG. 9B.

During the advance inspection, the specific size of the sight-target shown on display unit 112 may be the size that displayed on the electronic unit 110 while the detector 116 captures the predetermined indication. However, the specific size mentioned above may be the size that displayed on the electronic unit 110 of a previous predetermined time period during which the predetermined indication is received so as to reduce errors produced by response time of the inspected object.

In addition, during the advance inspection, if the predetermined indication in relative to the distinguish feature provided by the inspected object is different from the distinguish feature shown on the display unit 112, the electronic unit 110 may successively increase the size of the sight-target until the predetermined indication provided by the inspected object matches with the distinguish feature shown on the display unit 112 The electronic device 110 thereafter may successively display the sight-target with different distinguish features while the size of the sight-target is fixed at the specific size for several times for inspecting the visual acuity of the inspected object until all of the predetermined indications in relative to the distinguish features match the distinguish features successively shown on the display unit 112, and the specific sizes of the sight-targets now shown in the display 112 are defined as the visual acuity the inspected object. Therefore, the influence of erroneous movements of the inspected object on accuracy and inspection time can be effectively decreased.

After the visual acuity of left eye is identified, the electronic unit 110 then display the sight-target having an initial distinguish feature and an initial size (for example, the sight-target may have the size of 1 shown in Table 1) on the right-eye display zone 112R and successively increase the size of the sight-target until the detector 116 captures the predetermined indication. The distinguishing feature of the sight-target shown on the display 112 is then changed step by step while the size of the sight-target is fixed at the specific size, and the detector 116 captures eyesight information in relation to the changed distinguishing feature until the visual acuity inspection is accomplished.

In some embodiments, the virtual reality-based ophthalmic inspection system 10 may automatically inspect the visual acuity of the inspected object. In some embodiments, the virtual reality-based ophthalmic inspection system 10 may be coupled to a computer system 22 through the network 20 (as shown in FIGS. 9A and 9B) and perform the visual acuity inspection according to the instruction provided by ophthalmologists or optometrists at the remote end. In some embodiments, the virtual reality-based ophthalmic inspection system 10 may store the distinguishing feature identification information within the memory unit 118 and be coupled to the computer system 22 through network 20, ophthalmologists or optometrists at remote end receive the distinguishing feature identification information and then identify the visual acuity of the inspected subject according to their eyesight information.

The virtual reality-based ophthalmic inspection system 10 of the present disclosure accomplish rapid monocular visual acuity inspection by the preliminary and advance inspection. However, in some embodiments, virtual reality-based ophthalmic inspection system 10 may further determined whether the distinguish features of the sight-targets which the inspected subject are identified is the smallest size (as the size 1 shown in Table 1). As previously described, if the size of the sight-target shown on the display unit 112 of the electronic unit 110 is the smallest size, then the visual acuity of the inspected objected is 1.2; however, if the size of the sight-target shown on the display unit 112 of the electronic unit 110 is not the smallest size, the electronic unit 110 may reduce the size of the sight-target shown on the display 112 to further inspect the visual acuity to increase accuracy.

In some embodiments, the visual acuity is identified even if the inspected objected cannot identify all of the distinguish feature of the sight-target successively shown on the display unit 110 of the electronic unit 110. In such situation, the visual acuity of the inspected object is identified if the amount of the distinguish features of the sight-targets successively shown on the display 112 which are correctly recognized is greater than that are incorrectly recognized. On the contrary, of the amount of the distinguish features of the sight-targets successively shown on the display 112 which are correctly recognized is less than that are incorrectly recognized, that electronic unit 110 then increases the size of the sight-target until the amount of the distinguish features of the sight-targets which are correctly recognized is greater than that are incorrectly recognized.

Figure 10:
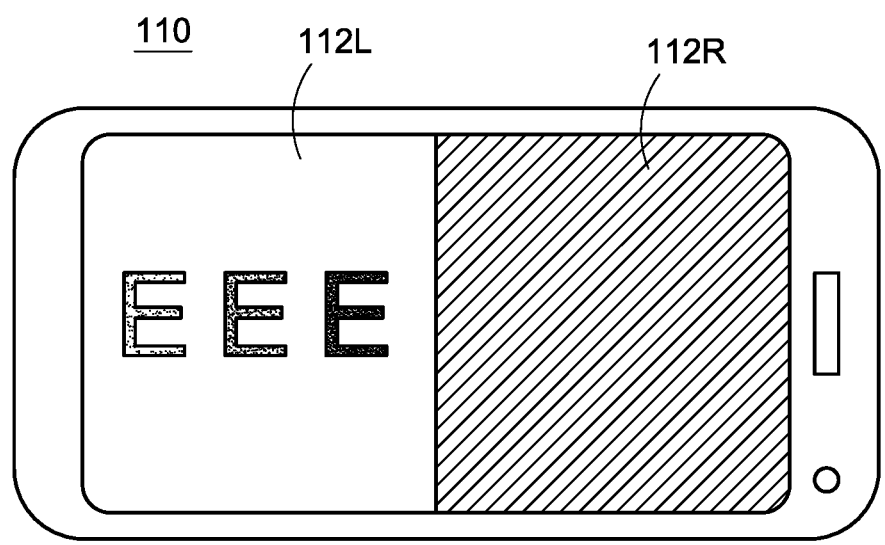
FIG. 10 depicts schematic diagrams illustrating eye sights shown on the display for inspecting visual sensitivity of left eye.

The virtual reality-based ophthalmic inspection system 10 of the present disclosure may further be configured to inspect the contrast sensitivity. Specifically, the electronic unit 110 may display a plurality of sight-targets arranged in line whose contrast varies from high to low on one of the left-eye display zone and the right-eye display zone for inspecting visual sensitivity, as shown in FIG. 10.

Figure 11:
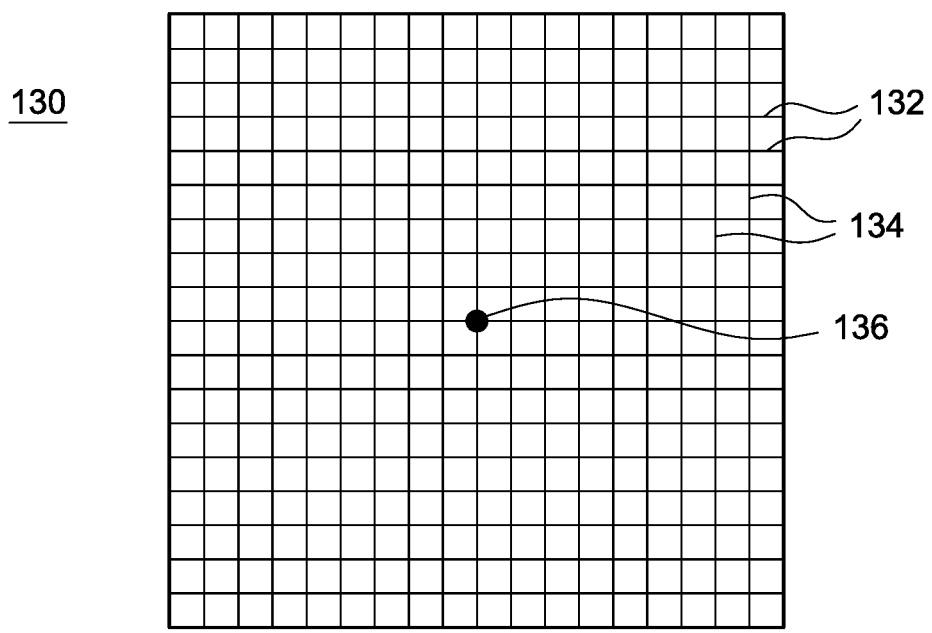
FIG. 11 depicts schematic diagrams illustrating the Amsler grid for inspecting macular degeneration of left eye.

The virtual reality-based ophthalmic inspection system 10 of the present disclosure may still further be configured to inspect the macular degeneration. Specifically, the electronic unit 110 may display an Amsler grid 130 on one of the left-eye display zone 112L and the right-eye display zone 112R to the left eye and the right eye of the inspected object to inspect the macular degeneration. FIG. 11 depicts schematic diagrams illustrating the Amsler grid 130 shown in the left-eye display zone 112L for inspecting macular degeneration of left eye. As can be seen in FIG. 11, the Amsler grid 130 is a square grid containing equally spaced, parallel horizontal lines 132, vertical lines 134, and a center point 136; the horizontal and vertical lines 132 and 134 collectively form a plurality of intersections, and the center point 136 is the geometric center of the Amsler grid 130.

Figure 12:
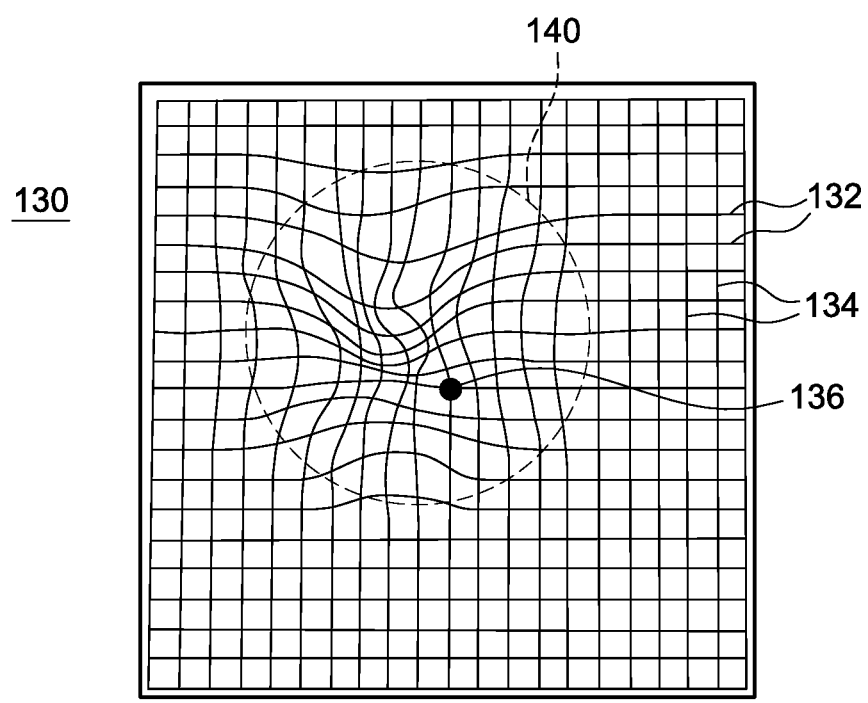
FIG. 12 depicts schematic diagrams illustrating the Amsler grid viewed by the inspected object having macular degeneration.

The inspected object is instructed to immediately report a preset indication (such as press button, voice indication or head rotation indication) in the severity or distribution of the distortion appear on the horizontal and vertical lines 132 and 134 of the Amsler grid 130, and the electronic unit 110 then identified that the inspected object has macular degeneration. During the inspection, the electronic unit 110 may further configured to position the portion of the Amsler grid 130 that the inspected object sees as distorted; the electronic device 110 may dichotomy the left-eye display zone 112L (or the right-eye display zone 112R) by brightness to acquire the portion of the Amsler grid 130 that the inspected object sees as distorted or unseen. In detail, if the distorted area is seen at the left portion of the left-eye display zone 112L, as shown in FIG. 12, then the electronic unit 110 may receive the preset indication (such as the inspected object's head turns left or a button pressed) to lower the brightness of the right portion of left-eye display zone 112L. Thereafter, if the distorted area is seen at the left-upper portion of the left-eye display zone 112L, then the electronic unit 110 may receive another preset indication (such as the inspected object's head lifts up or a button pressed) to lower the brightness of the lower portion of the left-eye display zone 112L. By applying the method continuously, the precisely position of the portion of the Amsler grid 130 that the inspected object sees as distorted is identified.

Figure 13:
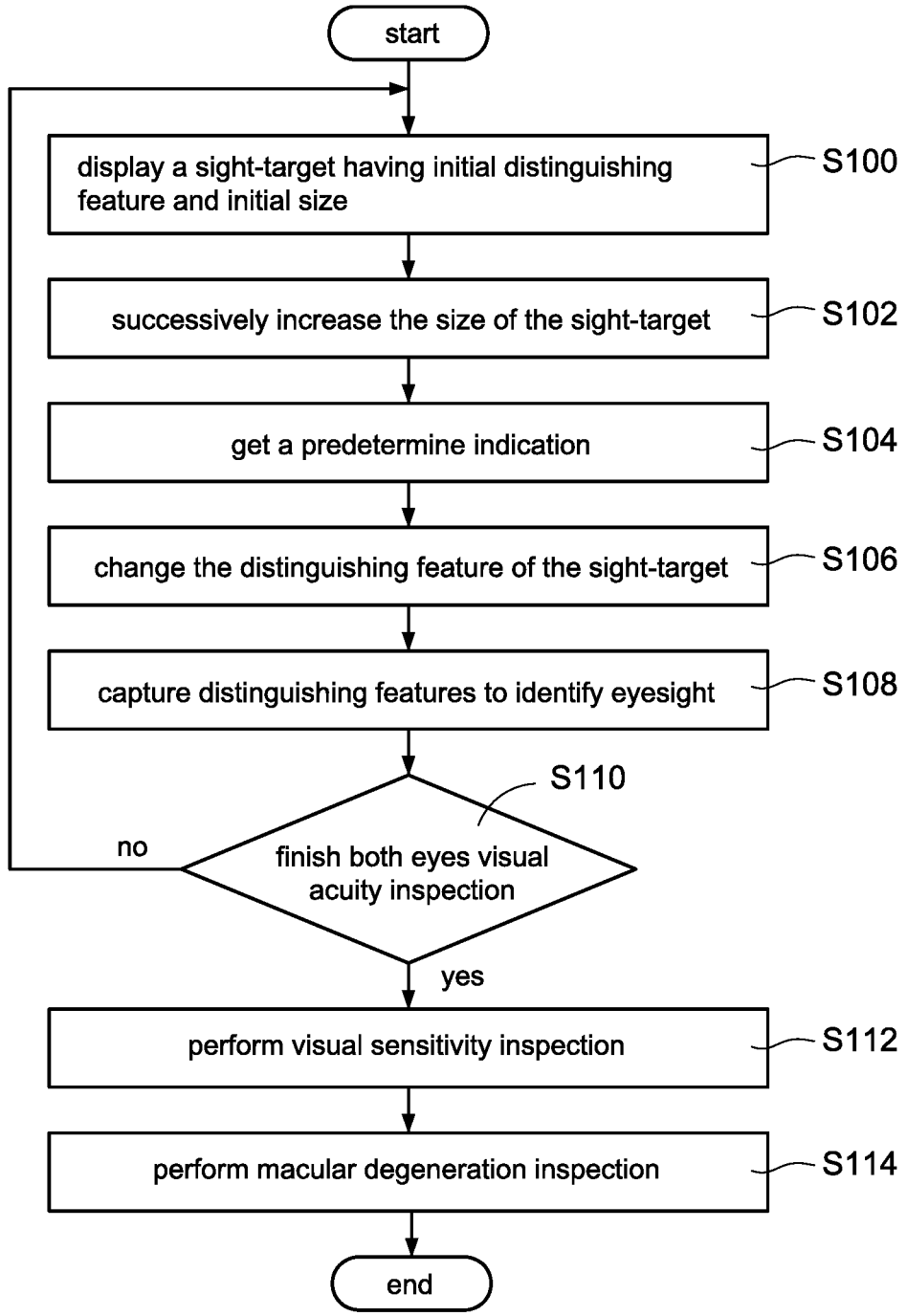
FIG. 13 depicts a flow chart of the ophthalmic inspection method in accordance with the present disclosure.

FIG. 13 depicts a flow chart of the ophthalmic inspection method in accordance with the present disclosure. The ophthalmic inspection method includes the following. First, providing a display unit 112 having a left-eye display zone 112L and a right-eye display zone 112R. Then, adjusting the brightness of the left-eye display zone 112L and the right-eye display zone 112R and display a sight-target with initial distinguish feature and initial size on one of the left-eye display zone 112L and the right-eye display zone 112R (step S100), wherein the initial size of the sight-target is in relation to the visual acuity of 1.2 listed on Table 1. The illuminance of the left-eye display zone 112L or the right-eye display zone 112R displaying the sight-target is designed to follow the standard protocols, for example, 200±120 cd/m², and the contrast between the sight-target and the background of the sight-target may be designed as 0.9±0.05 to enhance inspection accuracy. The left-eye display zone 112L or the right-eye display zone 112R does not display the sight-target is filled with black for complete blocking the vision of left eye or right eye:

Then, successively increasing the size of the sight-target while the distinguish feature is fixed as the initial distinguish feature (step S102) until capturing a predetermined indication (step S104) predetermined indication by at least one of body movements and voice.

Then, changing the distinguishing features of the sight-targets step by step while the size of the sight-target is fixed (step S106) and capturing eyesight information in relation to the distinguishing features (step S108). The specific size is the size that displayed on the display unit 112 while the system 10 captures the predetermined indication, i.e., the size mentioned in the step S104.

Then, determining whether both eyes visual acuity inspection is finished (step S110); if finished, inspecting contract sensitivity of the left eye and the right eye (step S112) and displaying the inspecting result (including the visual acuity and/or the contrast sensitivity) on the displaying unit 112 or storing the inspecting result in the memory unit 116, wherein the inspecting result stored in the memory unit 116 may be provided to ophthalmologists or optometrists at remote end for identifying the visual acuity and/or contrast sensitivity of the inspected subject. On the other hand, if both eyes visual acuity inspection is not finished, then displays the sight-target on the left-eye display zone 112L or the right-eye display zone 112R (step S100) and successively performs the step S102 to S108 until both eyes inspection are accomplished.

When performing the contrast sensitivity inspection, a plurality of sight-target arranged along a predetermined direction are shown on one of the left-eye display zone 112L or the right-eye display zone 112R. The contracts between the sight-targets and the background are different while the distinguish feature and the size thereof are the same for inspecting the contrast sensitivity of the left and right independently of the inspected object.

Last, inspecting macular degeneration of left eye and right eye independently (step S114). When performing macular degeneration inspection, the electronic device 110 may display an Amsler grid 130 on one of the left-eye display zone 112L and the right-eye display zone 112R, and dichotomy the left-eye display zone 112L (or the right-eye display zone 112R) by brightness to acquire the portion of the Amsler grid 130 that the inspected object sees as distorted or unseen.

Figure 14:
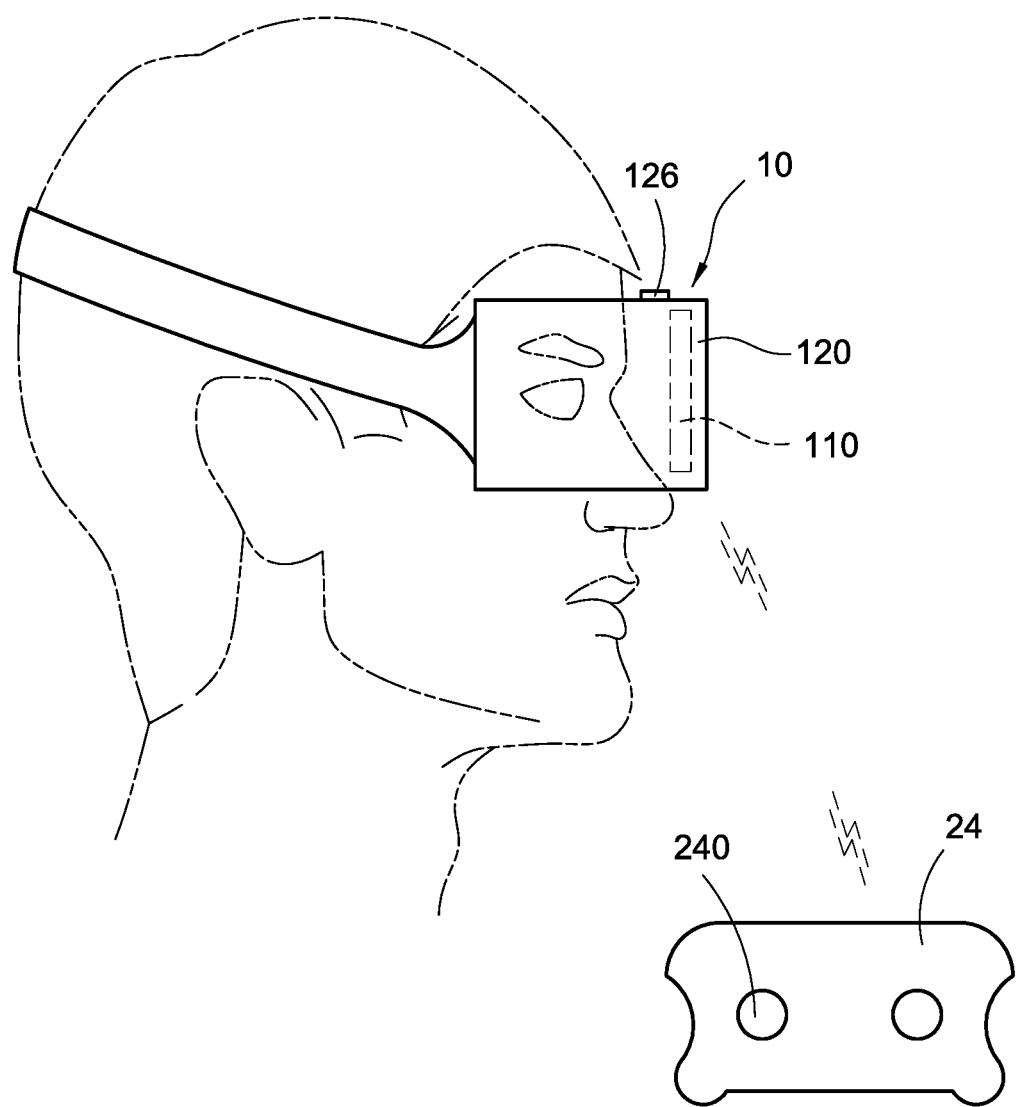
FIG. 14 depicts a schematic diagram illustrating a virtual reality-based ophthalmic inspection system in accordance with the present disclosure.

Notably, in an embodiment, the system 10 may capture the predetermined indication including at least one of body movements and voice by the detector 116 (as shown in FIG. 9A and FIG. 9b). In some embodiments, the predetermined indication may be provided by at least one button 126 disposed on the wearable unit 120 or a remote unit 20, wherein the remote unit 20 is wireless communication with the electronic unit 110, as shown in FIG. 14. Specifically, during the preliminary and advance inspection, the inspected object may press the button 126 on the wearable device 120 or the button 220 on the remote unit 20 while he/she can clearly identify the distinguish features of the sight-targets.

Although the present disclosure has been described with reference to the foregoing preferred embodiment, it will be understood that the disclosure is not limited to the details thereof. Various equivalent variations and modifications can still occur to those skilled in this art in view of the teachings of the present disclosure. Thus, all such variations and equivalent modifications are also embraced within the scope of the disclosure as defined in the appended claims.

What is claimed is:

1. A virtual reality-based ophthalmic inspection system comprising:
   a wearable unit, available for an inspected object to wear the wearable unit on head;
   an electronic unit, assembled with the wearable unit and having a left-eye display zone and a right-eye display zone, wherein the left-eye display zone is used for displaying at least one left-eye sight-targets, and the right-eye display zone is used for displaying at least one right-eye sight-targets; and
   at least one detector, disposed on the electronic unit,
   wherein during a visual acuity inspection and a right eye and a left eye are independently inspected, a sight-target with at least one distinguishing feature is shown on one of the left-eye display zone and the right-eye display zone, the left-eye display zone displays the sight-target while the right-eye display zone is filled with black, and the right-eye display zone displays the sight-target while the left-eye display zone is filled with black; a size of the sight-target is successively increased before the at least one detector captures a predetermined indication, after the at least one detector received the predetermined indication, the at least one distinguishing feature of the sight-target is changed step by step while the size of the sight-target is fixed at a specific size, the at least one detector further captures the distinguishing features to identify an eyesight information which relates the distinguishing features of the sight-targets successively displayed on the left-eye display zone or the right-eye display zone, and a visual acuity of the inspected object is identified according to the eyesight information.

2. The system of claim 1, wherein the specific size is the size that displayed on the electronic unit while the detector captures the predetermined indication.

3. The system of claim 1, wherein the specific size is the size that displayed on the electronic unit of a previous predetermined time period during which the predetermined indication is received.

4. The system of claim 1, wherein the left-eye display zone or the right-eye display zone displays a plurality of sight-targets whose contrast varies from high to low for inspecting visual sensitivity.

5. The system of claim 1, further comprising a background display calibration procedure for adjusting the illuminant and optimizing color temperature of the display unit.

6. The system of claim 1, wherein the sight-target initially displayed on the left-eye display zone and the right-eye display zone has a smallest size.

7. The system of claim 1, wherein the sight-target is selected from a set of letters consisting essentially of capital bold character E in a Berlin Sans FB font, capital character C in a Bauhaus 93 font, and lowercase character C in a Vrindab font.

8. The system of claim 1, further comprises:
   displaying an Amsler grid on one of the left-eye display zone and the right-eye display zone, and
   dichotomizing the left-eye display zone or the right-eye display zone shown with the Amsler grid by brightness to acquire the portion of the Amsler grid that the inspected object sees as distorted or impossible to see,
   wherein the Amsler grid comprises equally spaced, parallel horizontal lines, vertical lines, and a center point, the horizontal lines and the vertical lines collectively form a plurality of intersections, and the center point is the geometric center of the Amsler grid.

9. The system of claim 1, further comprising:
a button disposed on the wearable unit,
wherein the inspected object presses the button while clearly identifying the at least one distinguishing feature of the sight-target.

10. An ophthalmic examination method, comprising:
providing a display unit comprising a left-eye display zone and a right-eye display zone;
displaying a sight-target on one of the left-eye display zone and the right-eye display zone, wherein the sight-target has an initial distinguish feature and an initial size;
successively increasing a size of the sight-target while a distinguishing feature of the sight-target is fixed;
capturing a predetermined indication; and
successively changing the distinguish features of the sight-target while the size of the sight-target is fixed at a specific size and capturing an eyesight information in relation to the distinguishing features,
wherein during a visual acuity inspection and a right eye and a left eye are independently inspected, the size of the sight-target is successively increased before a detector captures the predetermined indication, after the detector received the predetermined indication, the distinguishing feature of the sight-target is changed step by step while the size of the sight-target is fixed at the specific size, the detector further captures the distinguishing features to identify the eyesight information which relates the distinguishing features of the sight-targets successively displayed on the left-eye display zone or the right-eye display zone, and a visual acuity of an inspected object is identified according to the eyesight information.

11. The method of claim 10, further comprising:
determining whether both eyes visual acuity inspection being finished;
displaying the sight-target on one of the left-eye display zone or the right-eye display zone, wherein the sight-targets has the initial distinguish feature and the initial size;
successively increasing the size of the sight-target while the distinguish feature being fixed;
capturing the predetermined indication; and
successively changing the distinguish features of the sight-targets while the size of the sight-target being fixed at a specific size and capturing eyesight information in relation to the distinguishing features.

12. The method of claim 11, further comprising:
identifying the visual acuity according to the distinguishing feature identification information.

13. The method of claim 11, further comprising:
storing the distinguishing features which response to eyesight information and the information remotely provides ophthalmologists or optometrists identifying the visual acuity.

14. The method of claim 11, further comprising:
displaying a plurality of sight-targets arranged in line whose contrast varies from high to low on one of the left-eye display zone and the right-eye display zone for inspecting visual sensitivity; and
capturing a contrast dentification information for inspecting the contrast sensitivity.

15. The method of claim 11, further comprising:
performing a background display calibration procedure for adjusting the illuminant and optimizing color temperature of the display unit.

16. The method of claim 10, further comprising:
displaying an Amsler grid on one of the left-eye display zone and the right-eye display zone, wherein the Amsler grid comprises equally spaced, parallel horizontal lines, vertical lines, and a center point, the horizontal lines and the vertical lines collectively form a plurality of intersections, and the center point is the geometric center of the Amsler grid; and
identifying the portion of the Amsler grid that the inspected object sees as distorted or unseen by capturing the predetermined indication to dichotomizing the display zone by contrast or brightness differences.

17. The method of claim 10, further comprising:
providing a button disposed on a wearable unit which is available for the inspected object to wear the wearable unit on head; and
pressing the button by the inspected object while clearly identifying the distinguish feature of the sight-target.

\* \* \* \* \*